United States Patent [19]
Nyqvist et al.

[11] Patent Number: 5,635,205
[45] Date of Patent: Jun. 3, 1997

[54] PHARMACEUTICAL CARRIER SYSTEM CONTAINING DEFINED LIPIDS

[75] Inventors: Håkan Nyqvist, Tullinge; Gert Ragnarsson, Bro; Per Tingvall, Norberg, all of Sweden

[73] Assignee: Pharmacia & Upjohn AB, Stockholm, Sweden

[21] Appl. No.: 307,761

[22] PCT Filed: Mar. 26, 1993

[86] PCT No.: PCT/SE93/00257

§ 371 Date: Nov. 23, 1994

§ 102(e) Date: Nov. 23, 1994

[87] PCT Pub. No.: WO93/19736

PCT Pub. Date: Oct. 14, 1993

[30] Foreign Application Priority Data

Mar. 27, 1992 [SE] Sweden .................. 9200952

[51] Int. Cl.$^6$ .................. A61K 9/127; A61K 9/16
[52] U.S. Cl. .................. 426/450; 424/489; 264/4.1; 428/402.2
[58] Field of Search .................. 424/450, 489; 428/402.2; 264/4.1, 4.3

[56] References Cited

U.S. PATENT DOCUMENTS

| | | | |
|---|---|---|---|
| 5,004,611 | 4/1991 | Leigh | 426/450 |
| 5,059,421 | 10/1991 | Loughrey | 424/417 |

FOREIGN PATENT DOCUMENTS

| | | |
|---|---|---|
| 0 158 441 A2 | 10/1985 | European Pat. Off. . |
| 87/07502 | 12/1987 | WIPO . |
| 92/05771 | 4/1992 | WIPO . |

OTHER PUBLICATIONS

Abstract—Stozek, et al., Pharmazie 44, pp. 466–468, 1989.

*Primary Examiner*—Gollamudi S. Kishore
*Attorney, Agent, or Firm*—Pollock, Vande Sande & Priddy

[57] ABSTRACT

A lipid carrier system for a local anaesthetic comprising a defined lipid system of at least two lipid components wherein at least one of the lipid components is amphiphatic and polar and one is nonpolar is provided. The system may further contain a hydrophilic solvent and additives or matrices for adapting it for administering to mucous membranes and for transdermally administering.

14 Claims, No Drawings

PHARMACEUTICAL CARRIER SYSTEM CONTAINING DEFINED LIPIDS

FIELD OF INVENTION

The present invention relates to a lipid carrier system for a local anaesthetic comprising a defined lipid system which includes at least two lipid components, wherein at least one of the lipid components is polar and amphiphatic and one is nonpolar. The system may further include a hydrophilic solvent and additives or matrices for adapting the system for administration to mucous membranes and for transdermal administration.

DESCRIPTION OF THE INVENTION

According to the invention the lipid carrier system, referred to as Biosome Forming Matrix (BFM), is characterized by a defined system of at least two defined lipid components chosen from classes of different polarity, of which at least one of the lipid components is brayer forming. By this is meant that discrete lipid particles, referred to as Biosomes, are formed spontaneously when the system interacts with excess aqueous media. This lipid system is also described in the International Patent Application WO 92/05771. By a defined lipid component is meant a lipid whose chemical composition is known and controlled. This will be explained in more detail below.

As before mentioned, at least one of the lipid components of the system is polar and amphiphatic and one is nonpolar. The amphiphatic and polar component is preferably phosphatidylcholine and the nonpolar is preferably chosen from the classes of mono-, di- and triglycerides or a mixture thereof.

The amount of the polar lipid class components will preferably be present in an amount that corresponds to 0.5–90 % (w/w) of the lipid system, preferably corresponding to the range of 5–50 % (w/w).

The property 'bilayer forming' is a well-known physical parameter and can be established readily with suitable physicochemical methods (e.g. surface balance method). The establishment of the formed discrete lipid particles can be done by physical and/or chemical methods, such as microscopy using polarized light, or diffraction methods.

The variation in the lipid composition provides the control mechanism by means of which Biosomes are formed and thereby also the rate at which Biosomes are formed which, will serve as a controlling factor for either immediate or sustained release of the entrapped or associated bioactive materials.

The lipid system according to the present invention can only be defined in the general terms set forth in claim 1. The difference between the matrix according to the invention and lipid systems that are already known to art resides in the ability of spontaneously forming Biosomes in contact with excess aqueous media. Thus, the inventive lipid system can be obtained by a) using well defined lipid components from at least two different lipid classes and by b) designing these lipid components into unique lipid matrices, which form Biosomes in vivo when interacting with water.

The following definitions are used in this document:
lipids—a general term for natural or synthetic compounds consisting of acyl carriers, such as glycerol, sphingosine, cholesterol, and others or derivatives thereof, to which one or more fatty adds are or can be linked. Similar molecules that contains a substantial hydrocarbon portion may also be included.

The lipids used for the Biosome Forming Matrices (BFMs) can be grouped in different lipid classes, depending on their polarity, namely:

nonpolar lipid classes—these have no polar head groups. Examples of nonpolar constituents are hydrocarbons, or non-swelling amphiphiles, such as mono-, di- and triacylglycerols, cholesterol, fatty alcohols or cholesterol esters.

polar lipid classes—these have polar head groups and possess surface activity, such as phospholipids or glycolipids. Depending on their specific interactions with water, they are subdivided further into the categories of swelling and soluble amphiphiles.

amphiphatic or amphiphilic lipid classes—such as phospholipids and glycolipids, being surface active.

bilayer forming lipid classes—amphiphatic lipids, such as PC (phosphatidylcholine), sphingomyelin, PI (phosphatidylinositol), with a molecular geometry that preferentially leads to bilayer structures in the presence of water.

The lipids used for the BFM consist of a mixture of lipid classes that are characterized by their different polarities. Polar lipids, such as phospholipids or glycolipids, and nonpolar lipids, such as mono-, di- and triglycerides, are the main constituents in the system although sterols, such as cholesterol, fatty acids, fatty alcohols and esters thereof as well as other lipid classes may also be used. This well defined mixture of lipids from different classes as defined above should not be confused with commercial products such as soybean oil, maize oil or soy lecithin and egg lecithin. In order to obtain the well defined lipid classes the commercial material, such as an oil or a lecithin, is fractionated and then the different lipid classes are admixed as explained in more detail in the examples below.

Furthermore, derivatives of lipids may also be used in combination with the above mentioned lipids. One example of this is polyethylene glycol coupled to phospatidylethanolamine, which has shown to prolong the circulation time of liposomes being injected into the blood stream. Another example of such a derivative is palmitoylcarnitine, which acts as an absorption enhancer for bioactive substances in the gut.

In the preferred way of initiating the formation of the BFM, the bioactive substance is admixed to a selected lipid, followed by admiring of a lipid of a different polarity. This polar/nonpolar alteration may be continued for as many cycles as necessary in the specific case, involving a range of lipids of different polarities.

The preferred way of incorporating a bioactive substance into the BFM is to admix the bioactive substance to amphiphilic lipids so as to create a homogeneous formulation, where the amount of amphiphilic lipids is generally in the total range of 0.5–90 % (w/w). Such an amphiphilic lipid will preferably be capable of spontaneous bilayer formation. Examples thereof are amphiphilic and polar lipid classes, such as phosphatidylcholine, phosphatidylglycerol, phosphatidylinositol or phosphatidylserine or mixtures thereof.

In order to prevent or to delay an immediate interaction of the amphiphile(s) with exogenous water, the system should also contain one or more lipids of the nonpolar lipid class. Examples of such nonpolar lipids are mono-, di- or triglycerols, cholesterol or its esters.

Endogenous water, ethanol or other solvents may be initially present in the system in small quantities (not sufficient for Biosome formation), if the bioactive substance needs such a solvent to be incorporated.

The design of the BFM includes not only the proper selection and/or combination of lipid classes, tailor-made for the solubilization of each bioactive substance, but also the proper selection of the distribution of fatty acids, i.e. the acyl groups attached to the lipid classes used. Variation of the acyl groups gives different physicochemical properties, as will be seen in the Examples below.

The rate by which the Biosomes are formed from the BFM in a given aqueous environment can be affected and controlled by varying the geometrical shape of the main bilayer forming lipid class, i.e. the effective head group area in relation to the steric conformation of the hydrocarbon tails.

A second way of affecting and controlling the formation of lipid particles is by varying the structure, thus the fluidity, of the hydrocarbon chains in the nonpolar part of the lipid system. This will affect the rate of interaction of the endogenous amphiphatic lipids and the exogenous aqueous medium.

Careful selection of lipid constituents for a specific BFM is required in order to incorporate a bioactive compound in vitro and to achieve a carrier system which can deliver the bioactive compound, such as local anaesthetics, to the tissues through mucous membranes, through the skin or when applied directly to a wound. The lipid system is also chosen so that lipid particles can be formed in excess aqueous media. This involves the selection of lipid classes as well as the distribution of the fatty acid residues and therefore requires access to analytically pure and well characterized lipids.

DETAILED DESCRIPTION OF THE INVENTION

According to the present invention the defined lipid system contains a drug which provides a systemic or local effect when administered transdermally or to mucous membranes or wounds. The drug is preferably a local anaesthetic such as lidocaine. The amount of the local anaesthetic is below 70% (w/w) of the formulation, preferably below 50% (w/w).

The BFM may also contain a given amount of a hydrophilic solvent, which can be water, glycerol, alcohols (e.g. ethanol), esters, or any mixture thereof. The amount in which the hydrophilic solvent is present is preferably low enough to avoid phase separation. This limit depends on the physical nature of the components of the BFM and has to be established for each individual system.

In the lipid particle forming matrix the discrete particles are formed spontaneously from the matrix without any chemical or physical treatment or initiation.

When preparing the BFM the amphiphatic and polar lipid or the nonpolar lipid is mixed with the bioactive material per se, or in solution, and preferably the nonpolar lipid or lipids are admixed to the mixture of the bioactive material and the amphiphatic and polar lipid or lipids.

The lipid particle forming matrix as defined above may be used in pharmaceutical compositions such as topical, rectal, nasal, vaginal, buccal, ocular vehicles, creams, or ointments and they may also be used in the manufacture of a pharmaceutical composition for rectal, nasal, intravaginal, buccal, ocular administration or administration locally to the skin, to wounds or to mucous membranes.

In a preferred composition according to the invention the BFM, as defined above, is adapted for topical use by optionally adding suitable vehicles for administration to tissues by application to the skin, to wounds or to mucous membranes.

In another preferred composition according to the invention, the BFM, as defined above, is applied on a porous cellulose matrix, which is adhesive to mucous membranes. Other types of matrices adhesive to mucous membranes made from natural or synthetic solid or semi solid polymers are well-known to all those skilled in this art and will be equally useful for the purpose intended here.

Examples 1-7 below illustrate the variation of the lipid constituents of the BFM in the absence of drugs, by selection of lipids and combination thereof without limiting the scope of protection.

Examples 8-11 describe the preparation of formulations of BFMs that contain lidocaine with the use of lipid constituents from Examples 1-7 and how in vivo tests have been performed with a pin-prick test.

Example 12 describes a pin-prick test performed with a commercial lidocaine ointment, used as a reference for comparison with formulations prepared according to Examples 8-11.

Example 13 describes the preparation of a formulation of a BFM manufactured from commercially available lipids and lidocaine and the results of a pin-prick test of such a formulation.

Example 14 describes the preparation of a formulation of a BFM with lipid constituents chosen from Examples 1-7, which is applied on a cellulose matrix for administration to the buccal mucosa. The example shows also how to perform an in vivo test with the formulation.

Example 15 describes the preparation of a formulation according to Example 14 with commercially available lipids.

Table 1 presents formulations prepared according to Examples 8-11.

Table 2 presents the results of the pin-prick tests performed with the formulations according to Examples 8-12.

Table 3 presents the results of the pin-prick test performed with the formulation prepared according to Example 13 for comparison with the results in Table 2.

Table 4 presents formulations prepared as described in Examples 14-15 and the results of pin-prick tests performed with these formulations.

The incorporation of drugs, as illustrated by lidocaine, in the defined lipid system is surprisingly advantageous. The results show that drugs incorporated in formulations based on the BFM, i.e. the defined lipid system, can be absorbed very rapidly. This is illustrated by a fast and high anaesthetic effect when lidocaine is administered transdermally, compared to a commercial lidocaine ointment. The extremely rapid effect is also observed after buccal administration.

Furthermore, variations in the ratio between the well-defined lipid constituents can also be used to control the absorption rate, which is another important aspect of the invention.

Another method of controlling the absorption is to vary the chain length of the glycerides. A preferred chain length is between six and eighteen carbon atoms. A person skilled in the art can readily modify the inventive compositions in a manner to obtain formulations to suit individual purposes.

Various modifications and equivalents will be apparent to the person skilled in the art and may be used in the compounds, compositions and methods of the present invention without departing from the concept or scope thereof, and it is therefore to be understood that the invention is not limited to the specific examples and embodiments described herein.

EXAMPLES

Example 1

1.25 g phospholipid from soybean (I) were added to 1.25 g of a glyceride mixture (II) and gently stirred for 12 h at 60°

C. 2.50 g of a triglyceride (III) were then added and the total mixture is stirred for 1 h at 60° C.

| Lipid class composition (g) | I | II | III | Fatty acid composition of triacylglycerol (wt %) | |
|---|---|---|---|---|---|
| Phosphatidylcholine | 0.50 | | | | |
| Phosphatidylethanolamine | 0.40 | | | | |
| Phosphatidylinositol | 0.23 | | | | |
| Nonpolar lipids | 0.12 | | | | |
| Monoacylglycerol | | 0.63 | | | |
| Diacylglycerol | | 0.63 | | | |
| Triacylglycerol | | | 2.50 | | |
| | | | | 8:0 caprylate | 58.5 |
| | | | | 10:0 caprate | 40.5 |
| | | | | 12:0 laurate | 0.6 |
| | | | | minors | 0.4 |
| Total | 1.25 | 1.25 | 2.50 | Total | 100 |

Example 2

1.25 g phospholipid from soybean (I) were added to 1.25 g of a glyceride mixture (II) and the mixture gently stirred for 12 h at 60° C. 2.50 g of a triglyceride (III) were then added and the total mixture was stirred for 1 h at 60° C.

| Lipid class composition (g) | I | II | III | Fatty acid composition of triacylglycerol (wt %) | |
|---|---|---|---|---|---|
| Phosphatidylcholine | 0.40 | | | | |
| Phosphatidylethanolamine | 0.35 | | | | |
| Phosphatidylinositol | 0.18 | | | | |
| Phosphatidic acid | 0.07 | | | | |
| Nonpolar lipids | 0.25 | | | | |
| Monoacylglycerol | | 0.63 | | | |
| Diacylglycerol | | 0.63 | | | |
| Triacylglycerol | | | 2.50 | | |
| | | | | 8:0 caprylate | 58.5 |
| | | | | 10:0 caprate | 40.5 |
| | | | | 72:0 laurate | 0.6 |
| | | | | minors | 0.4 |
| Total | 1.25 | 1.25 | 2.50 | Total | 100 |

Example 3

1.25 g phospholipids from soybean (I) were added to 1.25 g of a glyceride mixture (II) and the mixture gently stirred for 12 h at 60° C. 2.50 g of a triglyceride (III) were then added and the total mixture was stirred for 1 h at 60° C.

| Lipid class composition (g) | I | II | III | Fatty acid composition of triacylglycerol (wt %) | |
|---|---|---|---|---|---|
| Phosphatidylcholine | 0.50 | | | | |
| Phosphatidylethanolamine | 0.40 | | | | |
| Phosphatidylinositol | 0.23 | | | | |
| Nonpolar lipids | 0.12 | | | | |
| Monoacylglycerol | | 0.63 | | | |
| Diacylglycerol | | 0.63 | | | |
| Triacylglycerol | | | 2.50 | | |
| | | | | 16:0 palmitate | 10.0 |
| | | | | 18:0 stearate | 2.8 |
| | | | | 18:1 oleate | 20.6 |
| | | | | 18.2 linoleate | 58.9 |
| | | | | 18:3 linolenate | 6.7 |
| | | | | minors | 1.0 |
| Total | 1.25 | 1.25 | 2.50 | Total | 100 |

Example 4

1.25 g phospholipid from soybean (I) were added to 1.25 g of a glyceride mixture (II) and the mixture gently stirred for 12 h at 60° C. 2.50 g of a triglyceride (III) were then added and the total mixture was stirred for 1 h at 60° C.

| Lipid class composition (g) | I | II | III | Fatty acid composition of triacylglycerol (wt %) | |
|---|---|---|---|---|---|
| Phosphatidylcholine | 0.40 | | | | |
| Phosphatidylethanolamine | 0.35 | | | | |
| Phosphatidylinositol | 0.18 | | | | |
| Phosphatidic acid | 0.07 | | | | |
| Nonpolar lipids | 0.25 | | | | |
| Monoacylglycerol | | 0.63 | | | |
| Diacylglycerol | | 0.63 | | | |
| Triacylglycerol | | | 2.50 | | |
| | | | | 16:0 palmitate | 10.0 |
| | | | | 18:0 stearate | 2.8 |
| | | | | 18:1 oleate | 20.6 |
| | | | | 18:2 linoleate | 58.9 |
| | | | | 18:3 linolenate | 6.7 |
| | | | | minors | 1.0 |
| Total | 1.25 | 1.25 | 2.50 | Total | 100 |

Example 5

1.25 g phospholipid from soybean (I) were added to 1.25 g of a glyceride mixture (II) and the mixture gently stirred for 12 h at 60° C.

| Lipid class composition (g) | I | II |
|---|---|---|
| Phosphatidylcholine | 0.40 | |
| Phosphatidylethanolamine | 0.35 | |
| Phosphatidylinositol | 0.18 | |
| Phosphatidic acid | 0.07 | |
| Nonpolar lipids | 0.25 | |
| Monoacylglycerol | | 0.63 |
| Diacylglycerol | | 0.63 |
| Total | 1.25 | 1.25 |

Example 6

1.25 g phospholipid from soybean (I) were added to 1.25 g of a glyceride mixture (II) and 0.16 g ethanol. The total mixture was gently stirred for 6 h at 60° C. 0.16 g of a triglyceride (III) was added and the total mixture was stirred for another hour at the elevated temperature.

| Lipid class composition (g) | I | II | III |
|---|---|---|---|
| Phosphatidylcholine | 0.40 | | |
| Phosphatidylethanolamine | 0.35 | | |
| Phosphatidylinositol | 0.18 | | |
| Phosphatidic acid | 0.07 | | |
| Nonpolar lipids | 0.25 | | |
| Monoacylglycerol | | 0.63 | |
| Diacylglycerol | | 0.63 | |
| Triacylglycerol | | | 0.16 |
| Total | 1.25 | 1.25 | 0.16 |

Example 7

2.50 g phosphatidylcholine from soybean (I) and 7.50 g of a monoglyceride (II) were gently stirred for 6 h at 60° C. 1.25 g water were added and the stirring continued for a further hour at the elevated temperature.

| Lipid class composition (g) | I | II | Fatty acid composition of monoacylglycerol (wt %) | |
|---|---|---|---|---|
| Phosphatidylcholine | 2.50 | | | |
| Monoacylglycerol | | 7.50 | | |
| | | | 8:0 caprylate | 79.6 |
| | | | 10:0 caprate | 19.8 |
| | | | 12:0 laurate | 0.2 |
| | | | minors | 0.4 |
| Total | 2.50 | 7.50 | Total | 100 |

Example 8

Lipid formulation 1 was manufactured as follows:

7.75 g monoglyceride were heated to 60° C. and melted in a hot air oven. 1.75 g phosphatidylcholine were added and mixed gently until a homogeneous mixture was obtained at 60° C. 0.50 g lidocaine base was finally added and mixed gently at 60° C. until a homogeneous mixture was obtained. The mixture was then placed at 25° C. and allowed to cool.

Pin-prick test for local anaesthetic effect was performed as follows:

The skin of the underside of the forearms was washed gently with a cotton wool both containing ethanol 70% (v/v). 1 g of formulation 1 was applied with a spatula on a surface 20 mm in diameter and covered by an occlusive silicone adhesive (Tegaderm®). Three application sites were used.

Formulation 1 was also tested diluted with equal parts of water immediately before application and in this case 2 g were applied on three test sites respectively and covered by the occlusive adhesive.

Four subjects was included in the test series and the two test formulations were removed after 0.5, 0.75 and 1.0 h. The test areas were dried with a dry paper cloth immediately after removal of the occlusive adhesive and the anaesthetic score was tested by pricking with a sterile injection cannula 10 times blind to the subject. The number of unregistered pricks was receded and the anaesthetic score expressed as a precentage of the unegistered pricks.

Example 9

The same procedure was applied as that in Example 8.

Formulation 2: Monoglyceride 6.00 g, phosphatidylcholine 3.50 g and lidocaine base 0.50 g.

Formulation 2:1: Diluted Formulation 2 with an equal part of water immediately before application.

Pin-prick test: Four (4) test areas of Formulations 2 and 2:1 respectively. Formulations removed after 0.50, 0.75, 1.00 and 2.00 h. Two (2) subjects.

Example 10

The same procedure was applied as that in Example 8.

Formulation 3: Monoglyceride 5.00 g, phosphatidylcholine 3.50 g, water 1.00 g and lidocaine base 0.50 g.

Formulation 4: Monoglyceride 5.00 g, phosphatidylcholine 3.50 g, glycerol 1.00 g and lidocaine base 0.50 g.

Pin-prick test: Four (4) test areas of Formulation 3 and 4 respectively. Formulations removed after 0.50, 0.75, 1.00 and 2.0 h. Two (2) subjects.

Example 11

The same procedure was applied as that in Example 8.

Formulation 5: Monoglyceride 1.00 g and triglyceride 5.00 g were melted together at 60° C. Phosphatidylcholine 1.00 g added and finally lidocaine base 0.50 g.

Formulation 6: Monoglyceride 1.00 g and triglyceride 7.00 g were melted together at 60° C. Phosphatidylcholine 1.50 g was added and finally lidocaine base 0.50 g.

Pin-prick test: Three (3) test areas of Formulation 5 and 6 respectively. Formulations removed after 0.50, 1.00, and 2.00 h. Pin-prick test was performed on the test area with 2.00 h application time also at 3.00, 4.00, 6.00, 8.00 and 10.00 h after initial application. Six (6) test subjects.

Example 12

Formulation: Commercial lidocaine ointment 5% (Astra AB, Sweden).

Pin-prick test: 1.0 g applied on three (3) test areas. Six (6) test subjects. Formulation removed after 0.50, 1.00 and 2.00 h application time. Pin-prick test was also performed on the test site with 2 h application time also at 3.00, 4.00 and 6.00 hours after initial application.

Example 13

Medium chain monoglyceride (Imvitor®, Hüls) 6.00 g were melted at 60° C. in a hot air oven. Phosphatidylcholine 3.50 g (Sigma) were added and mixed gently. Lidocaine base 0.50 g was finally added and mixed gently for 5 hours at 60° C.

Pin-prick test: Three (3) test areas. Formulation removed after 0.50, 1.00 and 2.00 h. Two (2) subjects.

Example 14

Monoglyceride 1.00 g was melted together with triglyceride 5.00 g at 60° C. in a hot air oven until a homogeneous mixture was obtained. Phosphatidylcholine 3.50 g were then added and mixed gently to homogeneity. Finally lidocaine base 0.50 g was added and mixed gently until a homogeneous mixture was obtained.

A porous cellulose non-woven web (Wettex®, Teno AB, Sweden) 15 mm in diameter and 1 mm thick was soaked in the melted lipid formulation for 1 min and then allowed to cool at room temperature.

The cellulose web was administered to the inner chin mucosa on two (2) human volunteers and allowed to stay in contact with the buccal mucosa for 5 min. The web was then removed and local anaesthesia was tested by pricking with a sterile injection cannula 10 times. The number of unegistered pricks was recorded and the anaesthetic score expressed as the percentage of unregistered pricks.

Example 15

Same description as Example 14 but with the commercial lipid raw materials. Two (2) subjects in the pin-prick test.

TABLE 1

LIPID FORMULATIONS WITH LIDOCAINE TESTED IN-VIVO (PIN-PRICK)

| SUBSTANCE | FORMULATION % (w/w) | | | | | |
|---|---|---|---|---|---|---|
|  | 1 | 2 | 3 | 4 | 5 | 6 |
| LIDOCAINE BASE | 5 | 5 | 5 | 5 | 5 | 5 |
| MONOGLYCERIDE | 77.5 | 60 | 50 | 50 | 10 | 10 |
| PHOSPHATIDYLCHO-LINE | 17.5 | 35 | 35 | 35 | 35 | 15 |
| TRIGLYCERIDE (MEDIUM CHAIN) | — | — | — | — | 50 | 70 |
| WATER | — | — | 10 | — | — | — |
| GLYCEROL | — | — | — | 10 | — | — |

TABLE 2

PIN-PRICK TEST IN-VIVO (HUMAN) RESULTS

| TIME | ANAESTHETIC SCORE FOR FORMULATION | | | | | | | | |
|---|---|---|---|---|---|---|---|---|---|
| (h) | REF | 1 | 1:1* | 2 | 2:1* | 3 | 4 | 5 | 6 |
| 0 | 0 | 0 | 0 | 0 | 0 | 0 | 0 | 0 | 0 |
| 0.50 | 13 | 45 | 45 | 10 | 10 | 0 | 0 | 40 | 3 |
| 0.75 | — | 93 | 100 | 45 | 40 | 30 | 20 | — | — |
| 1.00 | 48 | 100 | — | 75 | 60 | 80 | 45 | 41 | 15 |
| 2.00 | 45** | — | — | 100 | 85 | 100 | 95 | 40** | 65** |
| 3.00 | 48 | — | — | — | — | — | — | — | 37 | 63 |
| 4.00 | 15 | — | — | — | — | — | — | 35 | 43 |
| 6.00 | 0 | — | — | — | — | — | — | 19 | — |
| 8.00 | — | — | — | — | — | — | — | 9 | 17 |
| 10.00 | — | — | — | — | — | — | — | 0 | 0 |

*Formulations 1 and 2 diluted with equal amount by weight of water. Two grams of diluted formulations 2 g were applied on the test area.
**Removal of formulations after 2 h application following pin-prick testing performed on the same test site on the skin.

TABLE 3

PIN-PRICK TEST WITH LIPID FORMULATION MANUFACTURED WITH COMMERCIAL LIPID QUALITIES
FORMULATION
Lidocaine base 5%, medium chain monoglyceride (Imvitor ®, Hüls) 60%, phosphatidylcholine (Sigma) 35%.
RESULTS

| TIME (h) | ANAESTHETIC SCORE |
|---|---|
| 0 | 0 |
| 0.50 | 10 |
| 1.00 | 40 |
| 2.00 | 50 |

TABLE 4

BUCCAL ADMINISTRATION LOCAL ANAESTHETICS FORMULATIONS

| SUBSTANCES | FORMULATION | |
|---|---|---|
|  | 1 | 2 |
| LIDOCAINE BASE | 5 | 5 |
| MONOGLYCERIDE (ACCORDING TO THE INVENTION) | 10 | — |
| PHOSPHATIDYLCHOLINE (ACCORDING TO THE INVENTION) | 35 | — |
| TRIGLYCERIDE (ACCORDING TO THE INVENTION) | 50 | — |
| MONOGLYCERIDE (HÜLS) | — | 10 |
| PHOSPHATIDYLCHOLINE (SIGMA) | — | 35 |
| TRIGLYCERIDE (HÜLS) | — | 50 |

| TIME | RESULTS ANAESTHETIC SCORE FOR FORMULATIONS | |
|---|---|---|
| (MIN) | 1 | 2 |
| 0 | 100 | 100 |
| 5 | 100 | 90 |
| 10 | 85 | 10 |
| 20 | 50 | 0 |
| 30 | 20 | 0 |

We claim:

1. A carrier system comprising a defined lipid system of at least two lipid components and a local anaesthetic, wherein i) at least one of the lipid components is amphiphatic and polar in an amount of 5–50% (w/w) of the lipid system, and ii) at least one of the lipid components is nonpolar and corresponding in an amount of 50 to 95% (w/w), and comprises a mixture of monoglycerides wherein the fatty acid portion of each of said monoglycerides is from an acid selected from the group consisting of 8:0 caprylic acid, and 10:0 capric acid, and wherein discrete lipid particles are formed spontaneously when interacting with excess aqueous medium.

2. System according to claim 1 wherein the aqueous medium further comprises glycerol.

3. System according to claim 1 wherein the amphiphatic and polar lipid components are bilayer forming selected from the group consisting of phospholipids and glycolipids.

4. System according to claim 3 wherein the amphiphatic and polar lipid component is a phosphatidylcholine.

5. System according to claim 1 wherein the nonpolar lipid component further comprises di-, or triglycerides have fatty acid components with chain lengths varying from six to eighteen carbon atoms.

6. System according to claim 1 wherein the nonpolar lipid component further comprises a member selected from the group consisting of:

i) a triglyceride with essentially a mixture of 8:0 caprylate and 10:0 caprate;

ii) a triglyceride with essentially a mixture of 18:2 linoleate, 18:1 oleate and 16:0 palmitate;

and mixtures thereof.

7. System according to claim 2 wherein the nonpolar lipid component further comprises di-, or triglycerides have fatty acid components with chain lengths varying from six to eighteen carbon atoms.

8. System according to claim 3 wherein the nonpolar lipid component further comprises di-, or triglycerides have fatty acid components with chain lengths varying from six to eighteen carbon atoms.

9. System according to claim 4 wherein the nonpolar lipid component further comprises di-, or triglycerides have fatty acid components with chain lengths varying from six to eighteen carbon atoms.

10. A pharmaceutical composition based on the system according to claim 1 wherein said system is combined with a solid or semi-solid polymer matrix, capable of being applied on mucous membrane.

11. System according to claim 3 wherein the nonpolar lipid component further comprises a member selected from the group consisting of:

i) a triglyceride with essentially a mixture of 8:0 caprylate and 10:0 caprate;

ii) a triglyceride with essentially a mixture of 18:2 linoleate, 18:1 oleate and 16:0 palmitate;

and mixtures thereof.

12. A pharmaceutical composition according to claim 8 characterized in that the local anaesthetic is lidocaine.

13. A method for administering an anaesthetic to a patient in need thereof which comprises transdermally administering or locally administering on a mucous membrane or wound of the patient, the pharmaceutical composition of claim 1.

14. The carrier system of claim 1 consisting essentially of said at least two lipid components and said local anaesthetic.

* * * * *